(12) United States Patent
Bergmann et al.

(10) Patent No.: US 8,507,210 B2
(45) Date of Patent: Aug. 13, 2013

(54) DETECTION OF BACTERIAL INFECTIONS IN SUBJECTS SUFFERING FROM DYSPNEA

(75) Inventors: Andreas Bergmann, Berlin (DE); Oliver Hartmann, Berlin (DE)

(73) Assignee: B.R.A.H.M.S GmbH, Henningsdorf (DE)

( * ) Notice: Subject to any disclaimer, the term of this patent is extended or adjusted under 35 U.S.C. 154(b) by 0 days.

(21) Appl. No.: 13/375,819

(22) PCT Filed: Jun. 4, 2010

(86) PCT No.: PCT/EP2010/003373
§ 371 (c)(1),
(2), (4) Date: Dec. 2, 2011

(87) PCT Pub. No.: WO2010/139475
PCT Pub. Date: Dec. 9, 2010

(65) Prior Publication Data
US 2012/0082998 A1    Apr. 5, 2012

(30) Foreign Application Priority Data
Jun. 5, 2009  (EP) ................................ 09162067

(51) Int. Cl.
*G01N 33/53*  (2006.01)
*G01N 33/567*  (2006.01)

(52) U.S. Cl.
USPC ............................. 435/7.1; 435/7.2; 435/7.21

(58) Field of Classification Search
None
See application file for complete search history.

(56) References Cited

U.S. PATENT DOCUMENTS
2010/0047835 A1  2/2010 Bergmann et al.

FOREIGN PATENT DOCUMENTS
WO      2008/040328 A2    4/2008

OTHER PUBLICATIONS

Morrison, L. K., et al., "Utility of a Rapid B-Natriuretic Peptide Assay in Differentiating Congestive Heart Failure from Lung Disease in Patients Presenting With Dyspnea," Journal of the American College of Cardiology, Jan. 16, 2002, vol. 39, No. 2, pp. 202-209, Elsevier, New York, NY; cited in International Search Report, dated Aug. 5, 2010, issued in corresponding PCT/EP2010/003373.

Rainer, T et al., "Diagnostic utility of CRP to neopterin ratio in patients with acute respiratory tract infections," The Journal of Infection, Feb. 2009, vol. 58, No. 2, pp. 123-130, Elsevier Ltd.; cited in international Search Report, dated Aug. 5, 2010, issued in corresponding PCT/EP2010/003373.

IP, Margaret, et al., "Value of serum procalcitonin, neopterin, and C-reactive protein in differentiating bacterial from viral etiologies in patients presenting with lower respiratory tract infections," Diagnostic Microbiology and Infectious Diseases, Oct. 1, 2007, vol. 59, No. 2, pp. 131-136, Elsevier Science Publishing Co., Amsterdam, NL; cited in International Search Report, dated Aug. 5, 2010, issued in corresponding PCT/EP2010/003373.

Delogu, G., et al., "Serum Neopterin and Soluable Interleukin-2 Receptor for Prediction of a Shock State in Gram-Negative Sepsis," Journal of Critical Care, Jun. 1995, vol. 10, No. 2, pp. 64-71, W.B. Saunders Company; cited in International Search Report, dated Aug. 5, 2010, issued in corresponding PCT/EP2010/003373.

Tarhan, D., et al, "Diagnostic value of neopterin in patients with active pulmonary tuberculosis and relation with CRP," Journal of Antimicrobial Agents, Mar. 1, 2007, vol. 29, p. S578, Elsevier Science. Amsterdam, NL; cited in Written Opinion, dated Aug. 5, 2010, issued in corresponding PCT/EP2010/003373.

International Search Report, dated Aug. 5, 2010, issued in corresponding PCT/EP2010/003373.

Written Opinion, dated Aug. 5, 2010, issued in corresponding PCT/EP2010/003373.

*Primary Examiner* — Albert Navarro
(74) *Attorney, Agent, or Firm* — Millen, White, Zelano & Branigan, P.C.

(57) ABSTRACT

The field of the present invention is the diagnosis and/or prediction and/or therapy follow-up of bacterial infections in subjects suffering from dyspnea. It is a subject of the present invention to provide a method for the diagnosis and/or prediction and/or therapy follow-up of bacterial infections in subjects suffering from dyspnea.

17 Claims, 7 Drawing Sheets

DETECTION OF BACTERIAL INFECTIONS IN SUBJECTS SUFFERING FROM DYSPNEA

The field of the present invention is the diagnosis and/or prediction and/or therapy follow-up of bacterial infections in subjects suffering from dyspnea. It is a subject of the present invention to provide a method for the diagnosis and/or prediction and/or therapy follow-up of bacterial infections in subjects suffering from dyspnea.

Heart failure (HF) is common, associated with high morbidity and mortality, and difficult to diagnose, particularly in the emergency department (ED) (Cleland et al.: *The Euro-Heart Failure survey programme—a survey on the quality of care among patients with heart failure in Europe. Part 1: patient characteristics and diagnosis. Eur Heart J* 2003, 24:442-63; Mosterd A., Hoes A. W.: *Clinical epidemiology of heart failure. Heart* 2007, 93: 1137-46). Dyspnea is the leading symptom of most HF patients. A major risk for these patients is the possible presence of a bacterial infection, respectively. Unfortunately, neither patient history nor physical examination can accurately differentiate dyspnea due to HF from dyspnea due to other causes, such as pulmonary diseases (Mueller C. et al.: *Emergency diagnosis of congestive heart failure: impact of signs and symptoms. Can J Cardiol* 2005, 21:921-4; Wang C. S. et al.: *Does this dyspneic patient in the emergency department have congestive heart failure? JAMA* 2005, 294:1944-56). However, accurate diagnosis is mandatory for the selection of the most appropriate treatment.

Procalcitonin (PCT) has become a well-established biomarker for sepsis diagnosis: PCT reflects the severity of bacterial infection and is in particular used to monitor progression of infection into sepsis, severe sepsis, or septic shock. It is possible to use PCT to measure the activity of the systemic inflammatory response, to control success of therapy, and to estimate prognosis (Assicot M et al.: *High serum procalcitonin concentrations in patients with sepsis and infection. Lancet* 1993, 341:515-8; Clec'h C et al.: *Diagnostic and prognostic value of procalcitonin in patients with septic shock. Crit Care Med* 2004; 32:1166-9; Lee Y J et al.: *Predictive comparisons of procalcitonin (PCT) level, arterial ketone body ratio (AKBR), APACHE III score and multiple organ dysfunction score (MODS) in systemic inflammatory response syndrome (SIRS), Yonsei Med J* 2004, 45, 29-37; Meisner M.: *Biomarkers of sepsis: clinically useful? Curr Opin Crit Care* 2005, 11, 473-480; Wunder C et al.: *Are IL-6, IL-10 and PCT plasma concentrations reliable for outcome prediction in severe sepsis? A comparison with APACHE III and SAPS II. Inflamm Res* 2004, 53, 158-163). The increase of PCT levels in patients with sepsis correlates with mortality (Oberhoffer M et al.: *Outcome prediction by traditional and new markers of inflammation in patients with sepsis. Clin Chem Lab Med* 1999; 37:363-368).

An increasing number of studies discuss the potential role of PCT in other infectious diseases like pneumonia, bacterial meningitis and malaria (Bugden S A, Coles C, Mills G D. *The potential role of procalcitonin in the emergency department management of febrile young adults during a sustained meningococcal epidemic. Emerg Med Australas* 2004, 16, 114-119; Chiwakata C B et al.: *Procalcitonin as a parameter of disease severity and risk of mortality in patients with Plasmodium falciparum malaria. J Infect Dis* 2001, 183, 1161-1164; Schwarz S et al.: *Serum procalcitonin levels in bacterial and a bacterial meningitis, Crit Care Med* 2000, 28, 1828-1832).

It is a desire in the art to predict a bacterial infection or sepsis which is undetectable by the use of PCT alone on the day of presentation. As a cut-off for the presence of a bacterial infection or sepsis, a level of >0.1 ng/ml PCT was chosen.

It is known that enhanced concentrations of neopterin in bodily fluids of patients are related to diseases in which cell-mediated immune response plays a role. Interferon-γ is produced in course of the immune response and stimulates the production and release of neopterin (Fuchs D. et al.: *Neopterin, biochemistry and clinical use as a marker for cellular immune reactions. Int Arch Allergy Immunol* 1993, 101:1-6).

The determination of neopterin reflects the state of activation of the cellular immunological system during the initial and subsequent stages of different diseases, and is of central significance. The determination of neopterin levels in human body fluids offers a useful innovative tool for monitoring diseases associated with the activation of cell-mediated immunity. As well as being of value in autoimmune diseases and in monitoring of immuno-stimulatory therapy the laboratory determination of neopterin is helpful in prognostication in HIV infection and in screening of blood donor samples (Murr C. et al.: *Neopterin as a marker for immune system activation. Curr Drug Metab* 2002, 3:175-87). Neopterin is a general marker for the activation of the cellular immune system.

Subject of the present invention is an in-vitro method of diagnosis and/or prediction and/or therapy follow-up of bacterial infections in subjects suffering from dyspnea, comprising the use of neopterin in combination with one or more cardiovascular or neurohumoral or cytokine markers.

Especially preferred is said in-vitro method for prediction of bacterial infections in a subject suffering from dyspnea or for prognosis of a bacterial infection in a subject suffering from dyspnea and/or a prediction or prognosis follow-up.

A preferred subject of the present invention is an in-vitro method of prediction of bacterial infections in a subject suffering from dyspnea or prognosis of a bacterial infection in a subject suffering from dyspnea and/or a prediction or prognosis follow-up, comprising the use of neopterin as a marker in combination with one or more marker selected from the group comprising cytokine and cardiovascular markers or neurohumoral markers or precursors or fragments thereof or fragments of said precursors.

For the above methods a sample may be taken from said subject in order to determine the respective markers.

In the in-vitro methods related to prognosis or prediction said subject does not have a bacterial infection at the time the sample is taken from said subject.

A subject is considered as not having a bacterial infection if the procalcitonin concentration in a sample selected from the group consisting of blood, serum and plasma taken from said subject is equal or less than 0.1 ng/ml, Assays for determining the procalcitonin level in a sample are well known in the art.

According to the present invention it was surprisingly shown that the combination of neopterin in combination with one or more cardiovascular or neurohumoral or cytokine markers may enhance considerably the efficiency of the diagnosis and/or prediction and/or therapy-follow up of bacterial infections in subjects suffering from dyspnea in comparison to state of the art diagnosis and/or prediction and/or therapy-follow up of bacterial infections in said subjects.

The combination of neopterin with one or more cardiovascular or neurohumoral or cytokine markers was especially efficient in all methods related to prognosis and prediction.

In an embodiment of the invention the in-vitro method according to the present invention comprises determining the level of neopterin and said one or more cardiovascular markers in a sample taken from said subject.

In an embodiment of the invention the in-vitro method according to the present invention comprises determining the level of neopterin and said one or more cardiovascular markers in a sample taken from said subject with one or more immunoassays.

According to the present invention said sample may be preferably selected from the group comprising a blood sample, a serum sample, and a plasma sample.

In one aspect if the invention the one or more cardiovascular markers are selected from MR-proADM, MR-proANP, CT-ProET-1, CT-proAVP, BNP and NT-proBNP and fragments thereof and/or precursors or fragments thereof of at least 12 amino acids.

The in-vitro method according to the present invention may comprise correlating the level of neopterin and said one or more cardiovascular markers and, based on the outcome of the correlation, determining whether said patient is suffering from a bacterial infection.

In one embodiment of the invention the bacterial infection is manifesting in a pneumonia. In another embodiment of the invention the bacterial infection is manifesting in a sepsis. It is well known in the art that one symptom of sepsis may be shortness of breath (Bozkurt and Mann 2003, *Circulation*, 108, e11-e13, page 2 right column, line 5 ff).

In a preferred embodiment of the in-vitro method according to the invention the cutoff value for neopterin is a level of >10 nmol/l.

In an especially preferred embodiment of the in-vitro method according to the invention the cutoff value for MR-proADM is >1 nmol/l, the cutoff value for CT-proAVP is >10 pmol/l, the cutoff value for CT-proET-1 is >100 pmol/l, the cutoff value for MR-proANP is >100 pmol/l, the cutoff value for NT-proBNP is >600 pg/ml, and the cutoff value for BNP is >280 pg/ml.

Another subject of the invention is the use of an assay for the determination of the level of neopterin and one or more cardiovascular markers in a sample, or an assay for the determination of the level of neopterin together with one or more assays for the determination of the level of one or more cardiovascular markers for detecting a bacterial infection.

Another subject of the invention is the above stated use for detecting a bacterial infection in a patient suffering from dyspnea.

Another subject of the invention is the above stated use for detecting a bacterial infection, wherein the bacterial infection is manifesting in a pneumonia.

Another subject of the invention is the above stated use for detecting a bacterial infection, wherein the bacterial infection is manifesting in a sepsis.

In a preferred embodiment of the above-mentioned uses for detecting a bacterial infection the cutoff value for neopterin is a level of >10 nmol/l.

The one or more cardiovascular markers according to said uses are preferably selected from MR-proADM, MR-proANP, CT-ProET-1, CT-proAVP, BNP and/or NT-proBNP and/or precursor or fragments thereof of at least 12 amino acids.

Preferably, the cutoff value for MR-proADM is >1 nmol/l, the cutoff value for CT-proAVP is >10 pmol/l, the cutoff value for CT-proET-1 is >100 pmol/l, the cutoff value for MR-proANP is >100 pmol/l, the cutoff value for NT-proBNP is >600 pg/ml, and the cutoff value for BNP is >280 pg/ml.

As it is shown in table I the combination of neopterin as marker (>10 nmol/l) with MR-proADM, CT-proET-1, CT-proAVP, MR-proANP, BNP or NT-proBNP resulted in a significantly enhanced efficiency of the of the diagnosis and/or prediction and/or therapy-follow up of bacterial infections in subjects suffering from dyspnea with respect to the odds ratio (see table 1).

The combination of neopterin with one or more marker selected from the group comprising cytokine and cardiovascular markers or neurohumoral markers or precursors or fragments thereof or fragments of said precursors, especially the combination of neopterin as marker with one or more marker selected from MR-proADM, MR-proANP, CT-proET-1, CT-proAVP, BNP and NT-proBNP and/or fragments thereof and/or precursors or fragments thereof of at least 12 amino acids, is especially efficient in the methods according to the present invention which are related to prediction and prognosis, see table 2. The values as displayed in table 2 are based on the same raw data as the values displayed in table 1. The chosen cut-offs according to table 2 resulted in an essentially identical negative predictive value for all marker and marker combinations, whereas the positive predictive value was significantly increased for the combination of neopterin with MR-proADM, MR-proANP, CT-proET-1, CT-proAVP, BNP or NT-proBNP compared to neopterin alone. Thus, the accordingly obtained positive predictive value is indicative for the prognostic power of the marker and combination of marker. As can been seen in table 2 the predictive power of the marker combinations is higher than for neopterin as marker alone. The predictive power of the combination of marker can also be drawn from table 1 when considering the odds ratio or relative odds ratio. The calculated sensitivity and specificity according to table 1 is not very indicative of the predictive power as both, sensitivity and specificity, are variable.

The diagnostic assay or assay or immunoassay can be of any type applied in the field of diagnostics, including but not restricted to assays methods based on     enzymatic reactions
    luminescence
    fluorescence
    radiochemicals The preferred detection methods comprise strip tests, radioimmunoassay, chemiluminescence- and fluorescence-immunoassay, Immunoblot assay, Enzyme-linked immunoassay (ELISA), Luminex-based bead arrays, and protein microarray assay.

The assay types can further be microtitre plate-based, chip-based, bead-based, wherein the biomarker proteins can be attached to the surface or in solution.

The assays can be homogenous or heterogeneous assays, competitive and non-competitive assays. In a particularly preferred embodiment, the assay is in the form of a sandwich assay, which is a non-competitive immunoassay, wherein the molecule to be detected and/or quantified is bound to a first antibody and to a second antibody. The first antibody may be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference). In the context of the present invention, capture molecules are molecules which may be used to bind target molecules or molecules of interest, i.e. analytes (i.e. in the context of the present invention the cardiovascular peptide(s)), from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules may for instance be selected from the group comprising a nucleic acid molecule, a carbohydrate molecule, a PNA molecule, a protein, an antibody, a peptide or a glycoprotein. Preferably, the capture molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

A sample in the meaning of the invention can be a biological fluid such as lymph, urine, cerebrospinal fluid, blood, serum, plasma, saliva, faeces, semen. The sample is collected from the patient or subjected to the diagnosis according to the invention.

Where appropriate, the sample may need to be homogenized, or extracted with a solvent prior to use in the present invention in order to obtain a liquid sample. A liquid sample hereby may be a solution or suspension.

Liquid samples may be subjected to one or more pre-treatments prior to use in the present invention. Such pre-treatments include, but are not limited to dilution, filtration, centrifugation, concentration, sedimentation, precipitation, dialysis.

Pre-treatments may also include the addition of chemical or biochemical substances to the solution, such as acids, bases, buffers, salts, solvents, reactive dyes, detergents, emulsifiers, chelators.

"Patients" or "subjects" in the meaning of the invention are understood to be all persons, irrespective whether or not they exhibit pathological changes, unless stated otherwise. In the meaning of the invention, any sample collected from cells, tissues, organs or the like can be a sample of a patient to be diagnosed. In a preferred embodiment the patient according to the invention is a human. In a further preferred embodiment of the invention the patient is a human suffering from dyspnea.

In the present invention, the term prediction denotes a prognosis of how a subject's (e.g. a patient's) medical condition will progress. This may include an estimation of the chance of recovery or the chance of an adverse outcome for said subject.

The sensitivity and specificity of a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e. apparently healthy) and "disease" populations (i.e. patients suffering from bacterial infections). For any particular marker, a distribution of marker levels for subjects with and without a disease will likely overlap. Under such conditions, a test does not absolutely distinguish normal from disease with 100% accuracy, and the area of overlap indicates where the test cannot distinguish normal from disease. A threshold is selected, above which (or below which, depending on how a marker changes with the disease) the test is considered to be abnormal and below which the test is considered to be normal. The area under the ROC curve is a measure of the probability that the perceived measurement will allow correct identification of a condition. ROC curves can be used even when test results don't necessarily give an accurate number. As long as one can rank results, one can create a ROC curve. For example, results of a test on "disease" samples might be ranked according to degree (e.g. 1=low, 2=normal, and 3=high). This ranking can be correlated to results in the "normal" population, and a ROC curve created. These methods are well known in the art (Hanley et al. 1982. *Radiology* 143: 29-36). Preferably, a threshold is selected to provide a ROC curve area of greater than about 0.5, more preferably greater than about 0.7, still more preferably greater than about 0.8, even more preferably greater than about 0.85, and most preferably greater than about 0.9. The term "about" in this context refers to +/−5% of a given measurement.

The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve is a measure of the probability that the measured marker level will allow correct identification of a disease or condition. Thus, the area under the ROC curve can be used to determine the effectiveness of the test.

The odds ratio is a measure of effect size, describing the strength of association or non-independence between two binary data values (e.g. the ratio of the odds of an event occurring in test negative group to the odds of it occurring in the test positive group).

The positive predictive value (PPV), or precision rate, is the proportion of patients with positive test results who are correctly diagnosed and/or predicted. It reflects the probability that a positive test reflects the underlying condition being tested for. The negative predictive value (NPV) is the proportion of patients with negative test results who are correctly diagnosed and/or predicted.

The total accuracy is the percentage of all patients classified correctly with the test.

The term "neurohumoral markers" in the context of the present invention is used for hormones and peptides including their precursors and fragments thereof influencing neuroendocrine systems that include but is not restricted to enkephalins, tachykinins, endorphins, dynorphin, oxytocin, vasopressin, adrenocorticotropin, cholecystokinin, rennin, angiotensin, vasoactive intestinal polypeptide, neuropeptide Y, calcitonin gene-related peptide, calcitonin, somatostatin, bombesin, neurotensin, corticotrophin-releasing hormone, thyrotropin-releasing hormone, gonadotropin-releasing hormone, catecholamines (e.g. norepinephrine, epinephrine, dopamine). The term "neurohumoral markers" includes all precursors thereof, fragments thereof and fragments of said precursors.

In the present invention the term "cardiovascular marker" is defined as a marker associated with the diagnosis and/or prognosis of cardiovascular diseases such as myoglobin, troponins T (cTnT) and I (cTnI), creatinine kinase MB (CK-MB), FABP, GDF-15, ST-2, procalcitonin (PCT), C-reactive protein (CRP), proAdrenomedullin and fragments thereof including midregional pro-adrenomedullin (MR-proADM), Adrenomedullin, PAMP, C-terminal proAdrenomedullin (CT-proADM), proEndothelin-1 and fragments thereof including C-terminal pro-endothelin-1 (CT-proET-1), big-Endothelin-1, Endothelin-1, NT-proEndothelin-1, proANP and fragments thereof including midregional pro-atrial natriuretic peptide (MR-proANP), N-terminal proANP (NT-proANP), ANP, proVasopressin and fragments thereof including C-terminal pro-arginine vasopressin peptide (CT-proAVP), Vasopressin, Neurophysin II, proBNP and fragments thereof including BNP and N-terminal proBNP (NT-proBNP). The term "cardiovascular marker" includes all precursors thereof, fragments thereof and fragments of said precursors.

A marker may be attributed to both groups, it may be a neurohumoral marker and a cardiovascular marker in case this marker influences the neuroendocrine systems and is associated with the diagnosis and/or prognosis of cardiovascular diseases.

In the present invention the term "cytokines" is defined as a protein that is secreted by specific cells of the immune system exerting immunomodulatory functions including lymphokines, interleukines and chemokines selected but not restricted to IL-6, IL-8, IL-10, TNF-alpha, IFN-gamma and IL-1 beta.

BRIEF DESCRIPTION OF THE FIGURES

FIGS. 1 to 7 show the Receiver Operating Characteristic (ROC) plots for neopterin and neopterin in combination with other markers. The true positive rate corresponds to the sensitivity, whereas the false positive rate corresponds to the expression: "-specificity"

Figure 1:
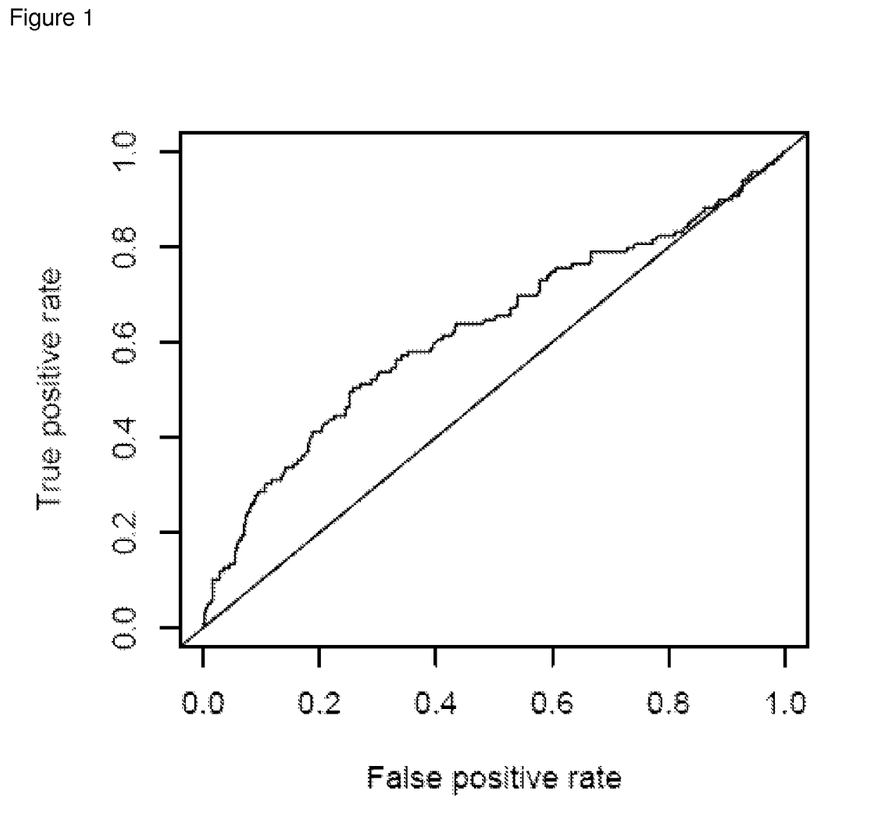
FIG. 1: ROC Plot for Neopterin. Area under the curve (AUC)=0.625 ($p<0.05$).
Figure 2:
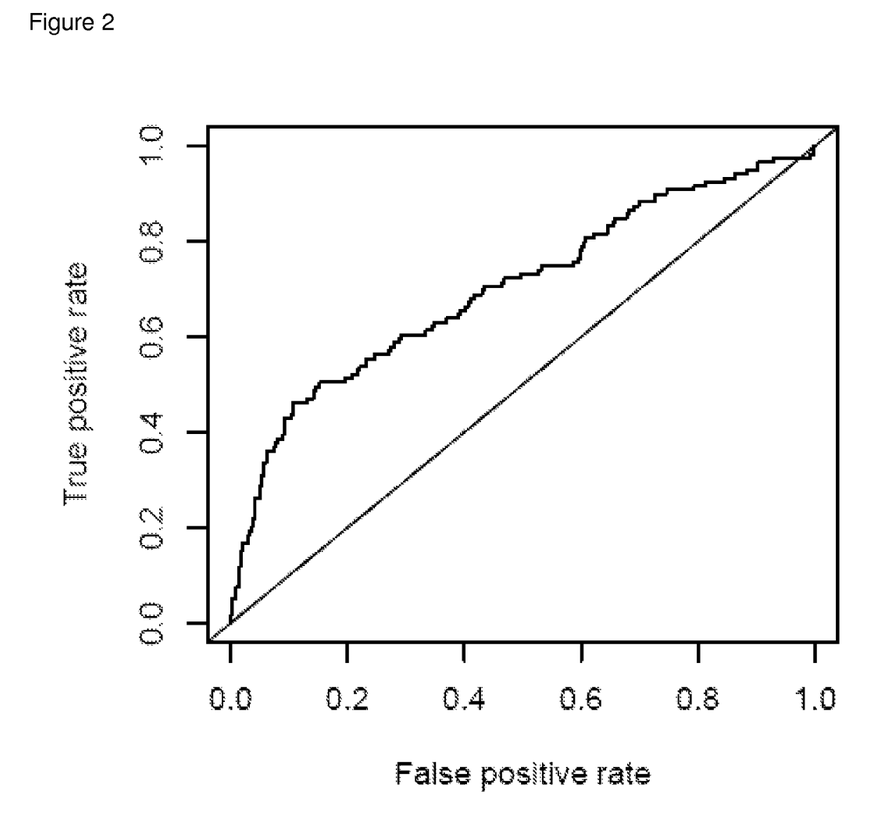
FIG. 2: ROC Plot for Neopterin plus (CT-proAVP). AUC=0.701 ($p<0.05$).
Figure 3:
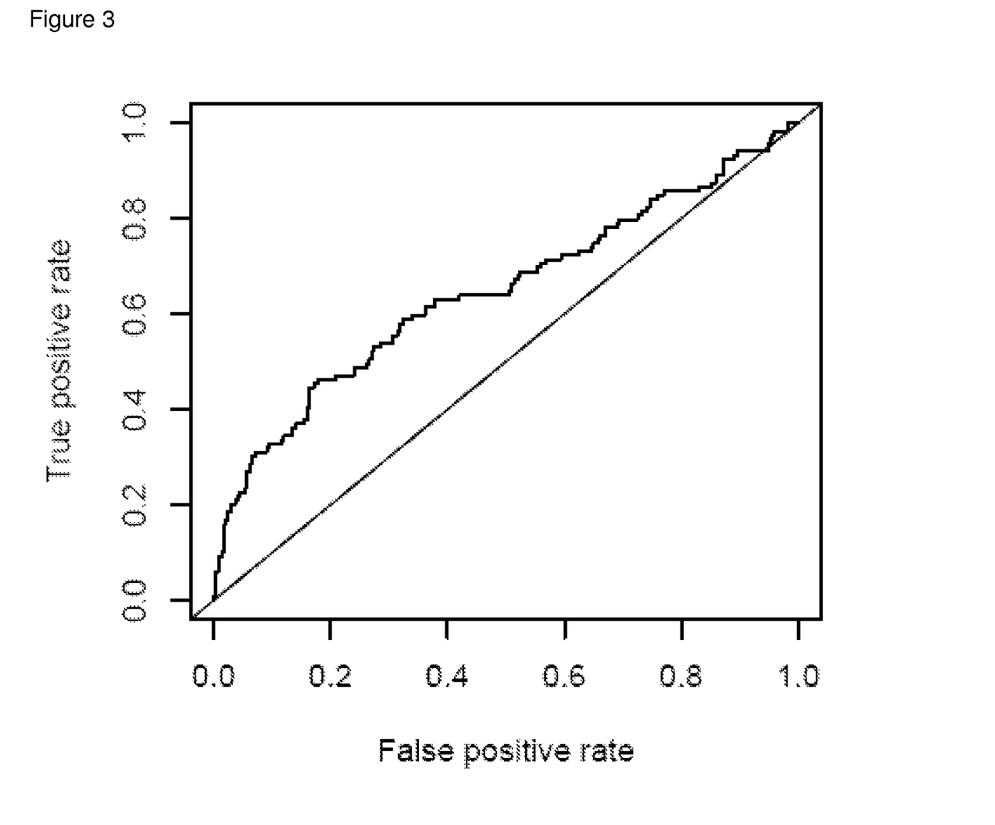
FIG. 3: ROC Plot for Neopterin plus MR-proANP. AUC=0.647 ($p<0.05$).
Figure 4:
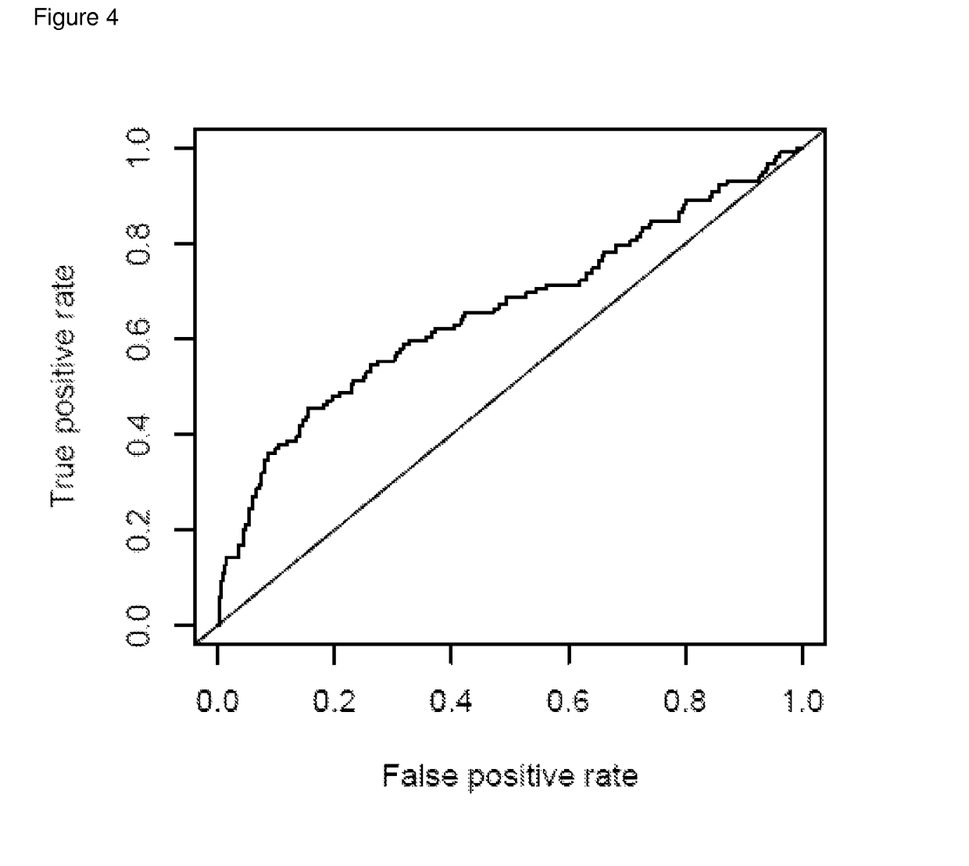
FIG. 4: ROC Plot for Neopterin plus MR-proADM. AUC=0.660 ($p<0.05$).
Figure 5:
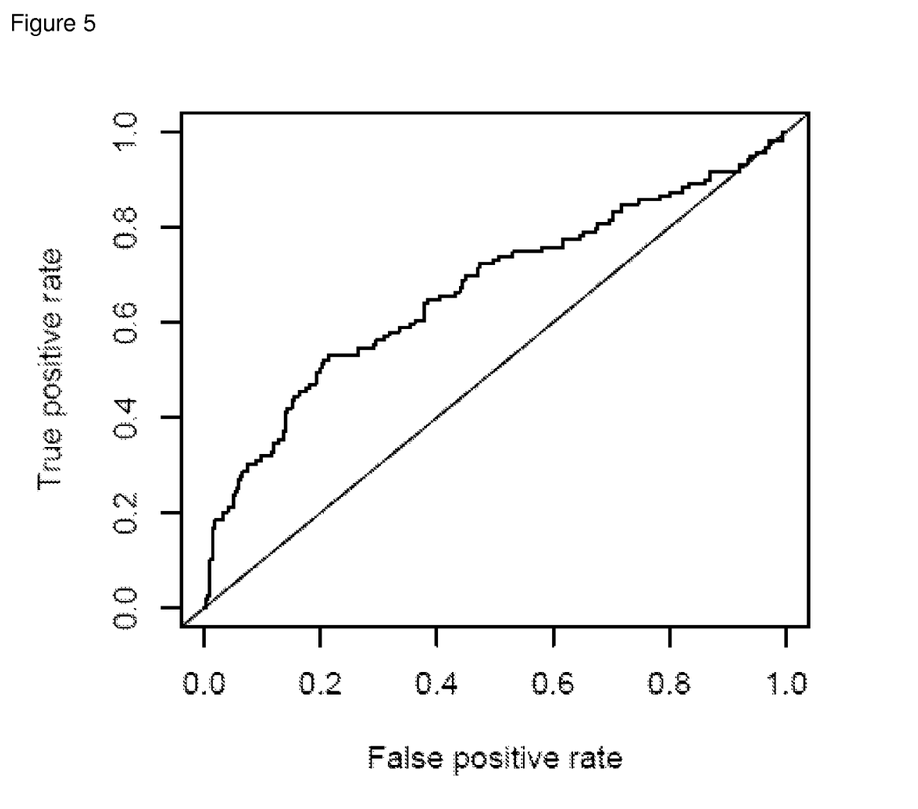
FIG. 5: ROC Plot for Neopterin plus CT-proET-1. AUC=0.668 ($p<0.05$).
Figure 6:
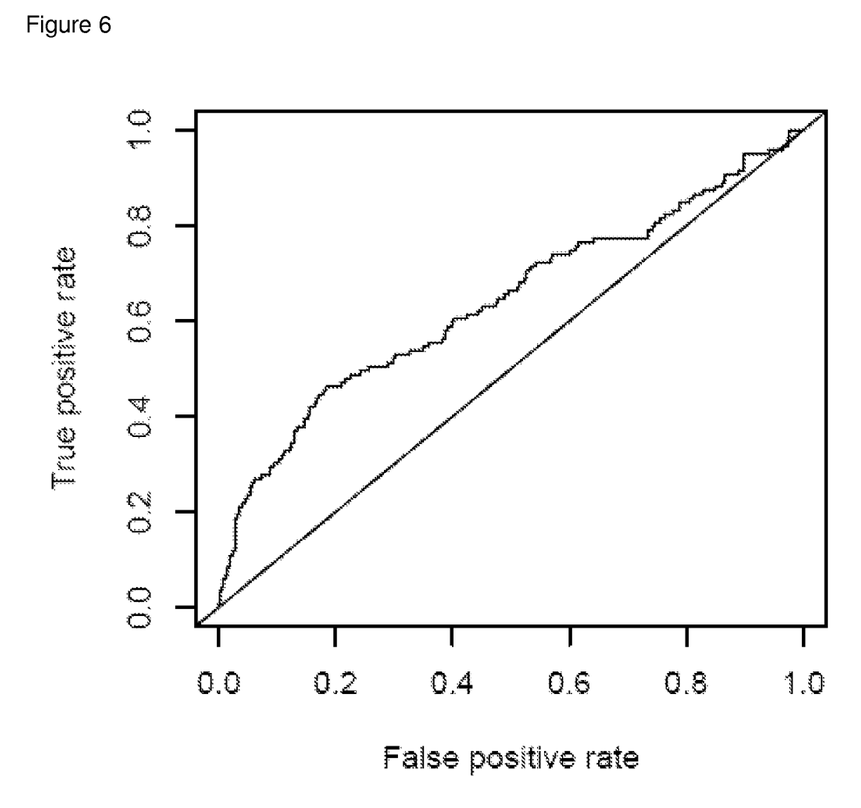
FIG. 6: ROC Plot for Neopterin plus BNP. AUC=0.640 ($p<0.05$).
Figure 7:
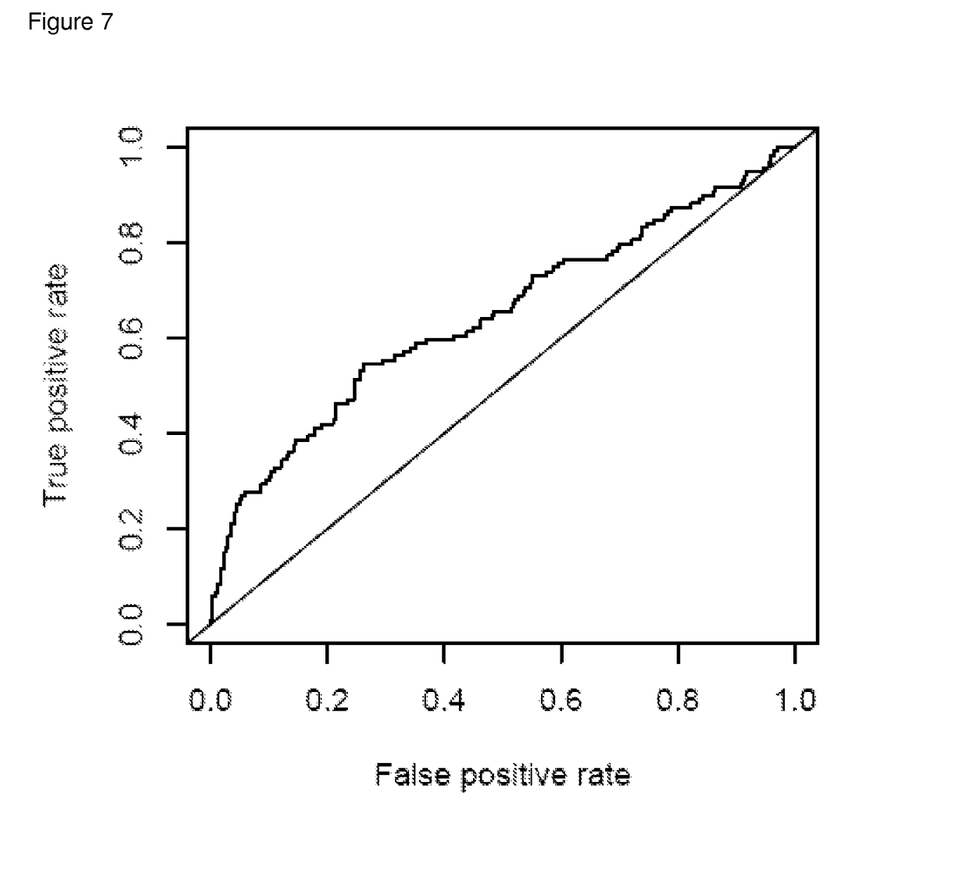
FIG. 7: ROC Plot for Neopterin plus NT-proBNP. AUC=0.646 ($p<0.05$).

EXAMPLES 964 emergency patients presented in the ED with symptoms of dyspnea and were subsequently hospitalized, mainly for congestive heart failure and pneumonia. A first blood sample was taken upon presentation in the ED and further one to three blood samples were taken during hospitalization.

The measurement of PCT was used to diagnose a bacterial infection with a cut-off value of 0.1 ng/ml.

Of 964 patients presented to the ED with symptoms of dyspnea, 428 did not develop a bacterial infection (group A) from presentation to the ED until discharge, as all PCT values measured over time were <0.1 ng/ml. In 416 cases (77,6%, group B) of the remaining 536 patients, the infection was already detectable by the use of PCT measurement (a level of >0.1 ng/ml PCT) upon presentation. The remaining 120 patients (22,4%, group C) out of the 536 patients group had low levels of PCT upon presentation (<0.1 ng/ml PCT) and PCT levels above 0.1 ng/ml at least on one follow-up measuring time point (day 1, day 3, day 5, at discharge) and were therefore defined as patients who developed a bacterial infection.

Neopterin is an unspecific marker for immunoactivation. The level of neopterin, measured at presentation to the ED, was increased in 60% of the patients from group C (>10 nmol/l). The same increase, however, leads to a number of false positive results in the prediction of infections in patient group A (42%/176 false positive).

Surprisingly, it has been shown that a combination of neopterin as a marker, with a cutoff value of >10 nmol/l, together with other markers measured at presentation to the emergency department and selected from mid-regional pro-Adrenomedullin (MR-proADM), C-terminal pro-endothelin 1 (CT-proET-1), C-terminal proVasopressin (CT-proAVP), mid-regional pro-atrial natriuretic peptide (MR-proANP), B-type natriuretic peptide (BNP) or N-terminal pro-B-type natriuretic peptide (NT-proBNP) resulted in a marked increase of the efficiency of infection prediction, with respect to the odds ratio, the positive predictive value (PPV) and the total accuracy (see table 1 and 2).

TABLE 1

| Model | Sensitivity | Specificity | Bacterial infection found in group C (n = 120) | false positive results in group A (n = 428) | odds ratio | relative Efficiency (rel. odds ratio) |
|---|---|---|---|---|---|---|
| neopterin >10 nmol/l | 60.5% | 58.9% | 73 | 176 | 2.2 | 100% |
| neopterin >10 nmol/l, MR-proADM >1 nmol/l | 48.3% | 79.2% | 58 | 89 | 3.6 | 164% |
| neopterin >10 nmol/l, CT-proAVP >10 pmol/l | 52.1% | 75.5% | 63 | 105 | 3.9 | 177% |
| neopterin >10 nmol/l, CT-proET-1 >100 pmol/l | 47.9% | 79.9% | 57 | 86 | 3.9 | 177% |
| neopterin >10 nmol/l, MR-proANP >100 pmol/l | 52.9% | 69.1% | 63 | 132 | 2.7 | 123% |
| neopterin >10 nmol/l, NT-proBNP >600 pmol/l | 51.3% | 71.7% | 61 | 121 | 3.0 | 136% |
| neopterin >10, BNP >280 pg/ml | 43.7% | 79.9% | 52 | 86 | 3.3 | 150% | overall $p < 0.05$

TABLE 2

| Model | true positive | false positive | true negative | total accuracy | positive predictive value | negative predictive value |
|---|---|---|---|---|---|---|
| neopterin >10 nmol/l | 73 | 176 | 252 | 59% | 29% | 84% |
| neopterin >10 nmol/l, MR-proADM >1 nmol/l | 58 | 89 | 339 | 72% | 39% | 85% |
| neopterin >10 nmol/l, CT-proAVP >10 pmol/l | 63 | 105 | 323 | 70% | 38% | 85% |
| neopterin >10 nmol/l, CT-proET-1 >100 pmol/l | 57 | 86 | 342 | 73% | 40% | 84% |
| neopterin >10 nmol/l, MR-proANP >100 pmol/l | 63 | 132 | 296 | 66% | 32% | 84% |
| neopterin >10 nmol/l, NT-proBNP >600 pmol/l | 61 | 121 | 307 | 67% | 34% | 84% |
| neopterin >10, BNP >280 pg/ml | 52 | 86 | 342 | 72% | 38% | 83% |

The invention claimed is:

1. An in vitro method for determining that a subject having dyspnea has a bacterial infection, for determining the prognosis of a subject suffering from dyspnea caused by a bacterial infection, and/or for determining follow-up prognosis of the progression of a bacterial infection in a subject having dyspnea, comprising detecting and quantitating, in a biological fluid sample from said patient, marker analytes selected from
   a) neopterin as a first marker, and
   b) at least one second marker selected from
      i) a cytokine,
      ii) a cardiovascular marker,
      iii) a neurohumoral marker,
      iv) a precursor of said second marker,
      v) a fragment of said second marker, and
      vi) a fragment of a precursor of said second marker,
   wherein said detection and quantitation comprises contacting said sample with a diagnostic assay capture molecule which binds to the marker analyte, and detecting and quantitating the capture molecule:analyte complex, thereby determining the amount of the analyte in the sample;
   wherein if the sample contains at least the minimum cutoff value for neopterin of >10 nmol/l, and the sample contains at least a marker-specific minimum cutoff value for a second marker, the subject having dyspnea is determined to have a bacterial infection, the prognosis for the subject having a bacterial infection is determined by the amount the level of the marker is over the cutoff value, and/or if the subject having dyspnea has had a prior sample subjected to said diagnostic assays, prognosis of the progression of a bacterial infection is determined by comparison of the values of the follow up diagnostic assays with the prior values;
   wherein if the sample does not contain at least a marker-specific minimum cutoff value of both first and second markers, the subject is determined to have dyspnea due to a cause other than a bacterial infection, and
   wherein said second marker-specific cutoff has been pre-determined to be the level at which the relative efficiency of prediction of bacterial infection by measuring both markers in combination is at least 23% greater than the efficiency of prediction of bacterial infection by measuring the level of neopterin alone.

2. The method of claim 1, wherein the second marker-specific cutoff is calculated using Receiver Operating Characteristic plots.

3. The method of claim 1, comprising determining the level of neopterin and said one or more cardiovascular markers.

4. The method of claim 1 comprising determining the level of neopterin and said one or more cardiovascular markers.

5. The method of claim 1, wherein said sample is a blood sample, a serum sample, or a plasma sample.

6. The method according to of claim 1, wherein said subject does not have a bacterial infection at the time the sample is taken from said subject.

7. The method of claim 6 wherein the second marker is procalcitonin, and the procalcitonin concentration determined in a sample of blood, serum or plasma is equal to or less than 0.1 ng/ml.

8. The method of claim 1, wherein the one or more cardiovascular markers are selected from MR-proADM, MR-proANP, CT-ProET-1, CT-proAVP, BNP and/or NT-proBNP and/or fragments thereof of at least 12 amino acids and/or precursors thereof.

9. The method of claim 1, wherein the bacterial infection is manifesting in a pneumonia.

10. The method of claim 1, wherein the bacterial infection is manifesting in a sepsis.

11. The method of claim 8, wherein the cutoff value for MR-proADM is >1 nmol/l, the cutoff value for CT-proAVP is >10 pmol/l, the cutoff value for CT-proET1 is >100 pmol/l, the cutoff value for MR-proANP is >100 pmol/l, the cutoff value for NT-proBNP is >600 pg/ml, and the cutoff value for BNP is >280 pg/ml.

12. The method of claim 1, wherein if the subject is determined to have or still have a bacterial infection, the need for further diagnostic testing and/or treatment of said infection is determined, or if the subject is determined to not have a bacterial infection, the need for further diagnostic testing and/or treatment for other causes of dyspnea is determined.

13. The method of claim 1, wherein if the subject is determined to have or still have a bacterial infection, additional diagnostic testing and/or treatment of said infection is prescribed, or if the subject is determined to not have a bacterial infection, further diagnostic testing and/or treatment for other causes of dyspnea is prescribed.

14. The method of claim 1, whereby additional diagnostic tests and/or a course of treatment of infection for the patient with dyspnea is prescribed based on the diagnosis of a bacterial infection, prognosis of the condition of the patient having a bacterial infection, and/or indication of the need for follow up treatment of a patient previously treated for a bacterial infection, or additional diagnostic tests and/or course of treatment of other causes of dyspnea are prescribed based on the diagnosed absence of a bacterial infection.

15. A method of claim 1, whereby dyspnea caused by a bacterial infection is differentiated from dyspnea caused by heart failure or a pulmonary disease.

16. A method of treating a subject with dyspnea who has been diagnosed with a bacterial infection, wherein the bacterial infection was diagnosed by detecting and quantitating in a biological fluid sample from said subject marker analytes selected from
  a) neopterin as a first marker, and
  b) at least one second marker selected from
    i) a cytokine,
    ii) a cardiovascular marker,
    iii) a neurohumoral marker,
    iv) a precursor of said second marker,
    v) a fragment of said second marker, and
    vi) a fragment of a precursor of said second marker,
  wherein said detection and quantitation comprises contacting said sample with a diagnostic assay capture molecule which binds to the marker analyte, and detecting and quantitating the capture molecule:analyte complex, thereby determining the amount of the analyte in the sample;
  wherein if the sample contains at least the minimum cutoff value for neopterin of >10 nmol/l, and the sample contains at least a marker-specific minimum cutoff value for a second marker, the subject having dyspnea is diagnosed with a bacterial infection; and
  wherein said second marker-specific cutoff has been predetermined to be the level at which the relative efficiency of prediction of bacterial infection by measuring both markers in combination is at least 23% greater than the efficiency of prediction of bacterial infection by measuring the level of neopterin alone;
  comprising administering to the subject an effective treatment for a bacterial infection.

17. An in vitro method for determining that a subject having dyspnea has a bacterial infection, for determining the prognosis of a subject suffering from dyspnea caused by a bacterial infection, and/or for determining follow-up prognosis of the progression of a bacterial infection in a subject having dyspnea, comprising
  detecting and quantitating, in a biological fluid sample from said patient, marker analytes selected from
    a) neopterin as a first marker, and
    b) at least one second marker selected from
      i) a cytokine,
      ii) a cardiovascular marker,
      iii) a neurohumoral marker,
      iv) a precursor of said second marker,
      v) a fragment of said second marker, and
      vi) a fragment of a precursor of said second marker,
    wherein said detection and quantitation comprises contacting said sample with a diagnostic assay capture molecule which binds to the marker analyte, and detecting and quantitating the capture molecule:analyte complex, thereby determining the amount of the analyte in the sample;
  wherein, if
    A. the sample contains at least the minimum cutoff value for neopterin of >10 nmol/l, and
    B. the sample contains at least a marker-specific minimum cutoff value for at least one second marker, wherein the second marker is a cardiovascular marker selected from MR-proADM, MR-proANP, CT-ProET-1, CT-proAVP, BNP and/or NT-proBNP and/or fragments thereof of at least 12 amino acids and/or precursors thereof, having a marker-specific cutoff value selected from, respectively:
      (i) MR-proADM >1 nmol/l;
      (ii) CT-proAVP >10 pmol/l;
      (iii) CT-proET1 >100 pmol/l;
      (iv) MR-proANP >100 pmol/l;
      (v) NT-proBNP >600 pg/ml; and/or
      (vi) BNP >280 pg/ml;
  the subject having dyspnea is determined to have a bacterial infection, the prognosis for the subject having a bacterial infection is determined by the amount the levels of the markers are over the cutoff values, and/or if the subject having dyspnea has had a prior sample subjected to said diagnostic assays, prognosis of the progression of a bacterial infection is determined by comparison of the values of the follow up diagnostic assays with the prior values; and
    wherein if the sample does not contain at least a marker-specific minimum cutoff value of both first and second markers, the subject is determined to have dyspnea due to a cause other than a bacterial infection.

* * * * *

UNITED STATES PATENT AND TRADEMARK OFFICE
CERTIFICATE OF CORRECTION

PATENT NO.      : 8,507,210 B2                                          Page 1 of 1
APPLICATION NO. : 13/375819
DATED           : August 13, 2013
INVENTOR(S)     : Bergmann et al.

It is certified that error appears in the above-identified patent and that said Letters Patent is hereby corrected as shown below:

In the Claims

Column 10, Line 22 reads: "of neopterin and said one or more cardiovascular markers."
Should read "of neopterin and said one or more cardiovascular markers with one or more immuneassays."

Signed and Sealed this
Tenth Day of December, 2013

Margaret A. Focarino
*Commissioner for Patents of the United States Patent and Trademark Office*